US006465502B1

(12) United States Patent
Bullock et al.

(10) Patent No.: US 6,465,502 B1
(45) Date of Patent: Oct. 15, 2002

(54) ADDITIONAL THERAPEUTIC USE

(75) Inventors: Gillian Rosemary Bullock, Uckfield (GB); Marc De Gasparo, Rossemaison (CH); Sabina Maria Ganter, Rheinhausen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/468,663

(22) Filed: Dec. 21, 1999

(30) Foreign Application Priority Data

Dec. 23, 1998 (EP) .......................................... 98811257

(51) Int. Cl.$^7$ ............................................. A61K 31/41
(52) U.S. Cl. ..................................................... 514/381
(58) Field of Search ......................................... 514/381

(56) References Cited

U.S. PATENT DOCUMENTS

| | | | |
|---|---|---|---|
| 5,225,428 A | 7/1993 | Kraemer et al. | 514/381 |
| 5,352,687 A | 10/1994 | Mueller et al. | 514/341 |
| 5,352,788 A | 10/1994 | Bernhart et al. | 544/231 |
| 5,399,578 A | 3/1995 | Buehlmayer et al. | 514/381 |
| 5,565,469 A | 10/1996 | Mihm et al. | 514/300 |
| 5,591,762 A | 1/1997 | IHauel et al. | 514/381 |
| 5,683,997 A | 11/1997 | Buehlmayer et al. | 514/213 |
| 5,684,015 A | 11/1997 | Mederski et al. | 514/303 |
| 5,811,445 A | 9/1998 | Corbier et al. | 514/398 |

FOREIGN PATENT DOCUMENTS

| | | |
|---|---|---|
| EP | 0 4 75 206 | 3/1992 |
| EP | 0 504 888 | 9/1992 |
| EP | 0 253 310 | 10/1994 |
| EP | 0 420 237 | 3/1996 |
| EP | 0 459 136 | 12/1996 |
| EP | 0 514 198 | 5/1998 |
| EP | 0 403 159 | 1/2000 |
| WO | WO 92/05784 | 4/1992 |
| WO | WO 93/20816 | 10/1993 |
| WO | WO 97/31634 | 9/1997 |
| WO | WO 9731634 A1 * | 9/1997 |

* cited by examiner

Primary Examiner—Theodore J. Criares
Assistant Examiner—Jennifer Kim
(74) Attorney, Agent, or Firm—Gregory D. Ferraro

(57) ABSTRACT

The invention relates to the use of an $AT_1$ receptor antagonist or or an $AT_2$ receptor modulator, respectively, or a pharmaceutically acceptable salt thereof, for producing a pharmaceutical preparation for the treatment of conditions or diseases associated with the increase of $AT_1$ receptors in the sub-epithelial area or increase of $AT_2$ receptors in the epithelia.

1 Claim, No Drawings

ADDITIONAL THERAPEUTIC USE

Angiotensinogen, an α2-macroglycoprotein, is cleaved by the enzyme renin into the decapeptide angiotensin I, which is itself only very slightly active biologically. In the next step of the cascade, two further amino acids are cleaved off by the action of the enzyme angiotensin converting enzyme (ACE), which is mainly bound in the endothelium, with the formation of angiotensin II. The latter is regarded as being one of the most powerful natural vasoconstrictors.

Angiotensin II interacts with specific receptors on the surface of the target cell. Success has by now been achieved in identifying receptor subtypes which are, for example, designated $AT_1$ receptors and $AT_2$ receptors. Studies on the renin-angiotensin system, particularly in relation to hypertension, have increased almost exponentially over the last decade. As a result, the number of receptors for Angiotensin II have now been identified and some of them have been cloned and analysed. Recently, considerable efforts have been made to identify the substances which bind to the $AT_1$ receptor, with active compounds of this nature frequently being termed angiotensin II antagonists. As a consequence of the inhibition of the $AT_1$ receptor, these antagonists can, for example, be employed as antihypertensives or for treating congestive heart failure.

The $AT_1$ and $AT_2$ receptors have also been studied for their distribution and biological properties and have been shown, despite a 30% homology, to have a very different distribution and activity.

The $AT_1$ receptor, which plays a major part in blood pressure regulation, has been found in the adrenal cortex, kidney, uterus etc. At a cellular level it has been found on fibroblasts, macrophages and smooth muscle cells (SMC).

In contrast, the $AT_2$ receptor has been found mainly in foetal tissues but also in adult especially in pathological tissue such as in ischaemic heart disease. Here it has been located on fibroblasts and endothelial cells.

The aim of the studies described hereafter is to evaluate the distribution of $AT_1$ and $AT_2$ receptors in the human lung using essentially the immunocytochemical and the in situ hybridisation methodologies.

Previously, specific antibodies have been made against epitopes of the $AT_1$ receptor but no such specific tools existed for the $AT_2$ receptor. Histological studies therefore depended on radio-labelled receptor antagonists together with autoradiography which only gave a relatively crude tissue localisation. In the last two years, however, specific well-characterised antibodies to the human receptor have become available and have therefore been used in the studies relied upon hereafter.

Methods and Materials

1. Antibody and in situ hybridisation (ISH) probe specificity and titration

In order to confirm the specificity of the immunocytochemical (ICC) and ISH studies, paraffin embedded blocks of normal human adrenal (cortex and medulla) are obtained from the archives of the Pathology Dept., University Hospital, Ghent, Belgium, and used as test material. $AT_1$ receptors are known to be predominantly located in the adrenal cortex and $AT_2$ in the medulla.

For the human lung studies, control material is obtained from autopsies where the patients have died from causes other than lung disease e.g. fatal accidents. Some of this material comes from Ghent as above, some from the archives of the Pathology Dept. of The Pennsylvania Hospital, Philadelphia, USA. Tissue containing small airways is selected as they appear to be more sensitive to injury.

All samples have been fixed in 10% buffered formalin as rapidly as possible post-mortem, dehydrated and embedded in paraffin wax. 3–5 µm sections are cut and mounted on silane coated glass slides.

In order to minimise any variations in the processsing, pairs of sequential sections are mounted on each slide, one for $AT_1$ and the other for $AT_2$ antibody exposure. Up to 20 slides are treated at the same time so that, with the exception of the primary antibody, al reagents including the chromogen are identical. Section thickness is therefore the only variable which could not be totally controlled.

2. Antibodies

Two $AT_1$ receptor antibodies, from Santa Cruz Inc., San Diego, Calf., USA, (clones N 10 and 306) are tested and found to give identical adrenal cortex receptor distribution.

The major part of the study is done with an $AT_2$ receptor antibody available from Santa Cruz (clone C18) which is tested and is found that it gives the identical staining pattern in adrenal medulla and lung as the first one.

All the antibodies have been rigorously tested by the commercial and individual suppliers for specificity and cross-reactivity.

3. ISH probes

PCR (Polymerase Chain Reaction) products were prepared and used as follows:

Oligonucleotides specific to human angiotensin II receptor type I (GenBank accession number M93394) and angiotensin II receptor type II (GenBank accession number U15592) were designed using the Oligo 5.0 software programme to homologous regions from both sequences (Table 1). cDNA from human bone tissue was prepared following standard methods (Sambrook J, Fritsch E F, Maniatis T. Molecular Cloning: a Laboratory Manual, 2nd Ed., Cold Spring Harbor Laboratory Press, Cold Spring Harbor, N.Y., 1989). For PCR the following oligonucleotide primer pairs were used: angiotensin II receptor type I, 5'-CTggCTgACTTATgCTTTTTACTgACT-3' (SEQ ID NO:1) and 5'-gATgCAggTgACTTTggCTACA-3' (SEQ ID NO:2); (PCR product size 236 base pairs) and for angiotensin II receptor type II, 5'-ATTTACTCCTTTTggC TACTCTTCCTC-3' (SEQ ID NO:3) and 5'-ggTCACggg TTATCCTgTTCTTC-3' (SEQ ID NO:4) (PCR product size 489 base pairs). PCR amplifications were performed with 10 ng of template cDNA using a MJ Research PCR Cycle machine and the following PCR cycles: 1) 94° C./2 min, 2) 94° C./10 sec, 60° C./30 sec, 72° C./15 sec for 35 cycles, using High Fidelity Taq polymerase (Boehringer Mannheim) with components provided in the manufacturer's kit. Products of the PCR amplifications were identified by electrophoresis through a 0.8% agarose/TBE gel (Sambrook J, Fritsch E F, Maniatis T. Molecular Cloning: a Laboratory Manual, 2nd Ed., Cold Spring Harbor Laboratory Press, Cold Spring Harbor, N.Y., 1989). To confirm the identity of the PCR amplification products, the DNA was eluted from the gel and cloned into the A/T cloning vector pMOSBlue (Amersham). Colonies containing a DNA insert of the correct size (Table 1) were fully sequenced on both strands to confirm their identity.

Each probe, both sense and anti-sense for the $AT_1$ and anti-sense only as described above, are labelled with fluorescin (FITC) and the presence of mRNA in the cells detected following hybridisation with the probe and use of a mouse anti-FITC probe plus the alkaline phosphatase anti-alkaline phosphatase (APMP) detection system. This labelling technique enhanced the detection of very low copy numbers.

4. Immunocytochemistry

For all the antibodies the procedure is as follows. 5 μm sections are first treated by antigen retrieval techniques, together with microwaving, in citrate buffer (pH 6.0).

Exposure is for 20 minutes and the slides left to cool down in the buffer. Where the antibodies are goat polyclonal, the peroxidase anti-peroxidase (PAP) method with diaminobenzidine (DAB) as chromogen is utilised, otherwise for rabbit polyclonals the APAAP system with new Fuchsin is used. The sections are first blocked with 1% bovine serum albumen (BSA) for 30 minutes to block non-specific receptors, followed by incubation with the primary antibody for 30 minutes at room temperature. Each antibody is titrated out and the optimal dilutions are as follows:

| Antibodies Used | Lung Tissue | Adrenal |
|---|---|---|
| $AT_1$ Clone N 10 | 1:200 | 1:500 |
| Clone N 306 | 1:200 | 1:500 |
| $AT_2$ Clone C 18 | 1:150 | 1:500 |

As a negative control, for the rabbit polyclonal a negative serum from Dako (Prosan, Ghent, Belgium) is used, for the goat polyclonal the primary antibody is omitted.

ISH

5 μm sections are deparaffinised and then exposed to 'in situ' hybridisation following well establised techniques. The sections are first treated with pre-hybridisation solution for 20 minutes at 55° C. They are then washed before exposure to the probes overnight at 55° C. After further washing, they are treated with a mouse anti-FITC antibody and the APAAP detection system for location of the specific message. For the $AT_1$ receptor, the sense probe is the negative control, for the $AT_2$ receptor, the probe is omitted.

Image analysis

In order to measure the stain intensity quantitatively, the slides are viewed in the Leica MR500 and the amount of stain per unit area of tissue recorded in pixels following Leica's instruction. This is done to establish the ratios of $AT_1$ to $AT_2$ receptor in different regions. These are a) airways epithelium, b) the sub-epithelial interstium, c) SMC around blood vessels and d) mucous glands.

RESULTS

Adrenal distribution studies $AT_1$ Distribution: All two antibodies give the following distribution pattern in the adrenal cortex, that is distinctive staining around the smooth muscle cells surrounding the blood vessels and also on the interstitial network on and around fibroblasts as predicted. There is no staining of endothelial cells.

$AT_2$ Distribution: The antibody is tested against adrenal medulla where strong staining of adrenal pheochromocytoma cells is seen.

ISH: Both antisense probes give a similar picture.

Control Lung $AT_1$ Distribution: Very clear staining of the interstitial cells underlying the airways epithelium (sub-epithelial) is seen and also the margins of the smooth muscle cell (SMC) surrounding the blood vessels. In addition macrophages are also positive.

$AT_2$ Distribution: This receptor appears to be strongly associated with the airway epithelial cells, with dense staining of the brush border. Positive cells are also seen in some of the mucous glands, on some vascular endothelial cells and on fibroblasts, chondrocytes and macrophages. There is no staining of SMC.

ISH: Again the probes give a similar picture. In particular the $AT_2$ probe give a strong signal on endothelial cells and on some mucous glands only.

Image analysis

The distribution of the protein and therefore the receptor as represented by stain intensity i.e. pixels per $\mu m^2$ of tissue is given in the following table.

| Antibody | Airway Epithelial | Sub-Epithelial | Glands | SMC |
|---|---|---|---|---|
| $AT_1$ | 0.00 | 8 | 0.00 | 10 |
| $AT_2$ | 5 | 0–1 | 5 | 0.00 |

The presence of Angiotensin II receptors in adrenal cortex and medulla has previously been demonstrated by both biochemical and histological means. The data are obtained with both commercially available and privately supplied antibodies both confirming these findings but also establishing the reliability of the instant immunocytochemical and ISH methodology.

In view of the results of these studies, the distribution of the $AT_1$ and $AT_2$ receptors in normal and diseased lung tissues has to be compared, in order to determine the specific $AT_1$ and $AT_2$ distributions and ratios.

The presence of $AT_1$ receptors in the lung has previously been shown biochemically and now their exact cellular location has been demonstrated. This information is vital for establishing the proportions of $AT_1$ and $AT_2$ receptors in different regions of the lung under normal and pathological conditions.

The data on the distribution especially of the $AT_2$ receptor is totally new as no previous data exist as to their presence or distribution. Several important points arise from this study.

First the presence of the $AT_2$ receptor on the bronchial epithelial cells of the small airways. As it is already known this receptor is considered to be anti-fibrotic, anti-proliferative and pro-apoptotic. Therefore up- or down-regulation on epithelial cells has profound effects on epithelial cell replacement, development of hyperplasia and even a role in the development of lung cancer.

Secondly, the presence of considerable amounts of the protein on the brush border of the epithelial cells could well be associated with the amount of mucous secretion as some of the epithelial cells of the mucous glands have also been shown to carry the receptor. From the ISH data, some glands contain a high level of mRNA.

Finally, the presence of the $AT_2$ receptor on vascular endothelial cells has now been confirmed both by immunocytochemistry and in situ hybridisation. Its distribution to be both infrequent and not on all the cells of one particular vessel hasbeen found.

These studies confirm and extend existing data on the presence and distribution of Angiotensin II type $AT_1$ and $AT_2$ in the human lung. The presence of the $AT_2$ receptor on the small airway epithelial cells has considerable consequences for the understanding of diseases arising from alteration in the function of these cells.

Very little is known on the localisation of the AT receptors in the human lung and about their distribution, up or down regulation and ratio in normal and diseased lung tissue. For this study, samples are collected from normal lung, and from patients with chronic obstructive pulmonary disease (COPD)± hypertension.

Lung samples

These have been obtained from the following groups of patients all clinically defined.

| | | |
|---|---|---|
| NN | (n = 3) | non-smokers, normal tissue |
| C | (n = 5) | smokers but otherwise normal |
| COPD | (n = 8) | COPD positive, normal BP |
| COPD/H | (n = 3) | COPD plus hypertension |
| H | (n = 4) | smokers with raised BP |

The airways are carefully dissected out of the lungs immediately after removal of the lung from the patient for tumour resection or other reasons. The region is carefully selected to be free of any cancerous tissue. The small blocks are then fixed in 4% paraformaldehyde for 2 h at room temperature before embedding in paraffin wax. This is to ensure optimum structural integrity and retention of antigenic activity.

Methods for establishing receptor localisation a) Immunocytochemistry (ICC). 2×$AT_1$ antibodies are tested, Santa Cruz (clones N-10 and 306). One $AT_2$ antibody has also been tested, Santa Cruz (clone C 18).

Digital images show:

Distribution of the $AT_2$ receptor in bronchiolar epithelial cells including the brush border and on the mucous gland cells.

Adjacent section stained for $AT_1$ receptor illustrating the very different distribution on smooth muscle cells, fibroblasts/stroma and macrophages.

Analysis of human lung from patients

All material obtained to date has been sectioned and stained by ICC for both $AT_1$ and $AT_2$ receptor localisation with appropriate negative controls. Image analysis has been started with readings from one section per patient to date (this is a slow process as base lines have to rigidly adhered to). Measurements have been made of the epithelial v subepithelial and blood vessel. This analysis is being done in a "blinded" manner so that no comment can be made other than the fact that some "patients" clearly have levels well away from the average. Discrepancies due to varying section thickness and staining have been minimised by doing the $AT_1$ and $AT_2$ ICC simultaneously with sequential sections. Thus the same batch of chromogen could also be used.

The findings of a lung epithelial localisation for the $AT_2$ receptor has a number of consequences. As this receptor has been shown to be both anti-proliferative, anti-fibrotic and pro-apoptotic its up-regulation is anticipated to have consequences for a number of lung diseases; e.g. that smoking alone has any influence. It is a role in such fibrotic conditions as adult respiratory distress syndrome (ARDS), or even in reducing the proliferative capacity of the epithelium in lung cancer.

Results

Receptor localisation

All the antibodies and riboprobes are tested on normal adrenal cortex and medulla where both receptor types are known to be present in relative abundance.

The process is repeated on normal lung tissue where we are able to detect both $AT_1$ and $AT_2$ receptors and their mRNA. The localisation is as follows:

$AT_1$—on smooth muscle cells, fibroblasts/stroma, macrophages. This is fairly predictable except the intensity and number of receptors in normal lung is quite high.

$AT_2$—on bronchial epithelial cells (especially the brush border), on mucous glands (some). In addition, on the vascular endothelial cells, fibroblasts, macrophages and cartilage cells.

This is a totally unexpected and novel finding which needs investigating further. The epithelial cell and mucous gland location is confirmed by both protein and mRNA content, the brush border location relates to mucous secretion.

DISTRIBUTION OF ANGIOTENSIN $AT_1$ AND $AT_2$ IN THE LUNGS OF PATIENTS WITH CHRONIC BRONCHITIS COMPARED WITH CONTROLS

| | Epithelial | | Sub-epithelial | | Ratio $AT_1$ (Epithelia)/ $AT_2$/ |
|---|---|---|---|---|---|
| Group | $AT_1$ | $AT_2$ | $AT_1$ | $AT_2$ | (Sub-epithelial) |
| Control (1) Smokers - N = 4 | 0.02 | 7.15 | 4.07 | 0.01 | 0.56 |
| Control (2) Non-Smokers N = 5 | 0.02 | 9.49 | 6.45 | 1.3 | 0.67 |
| Control (3) Smokers Hypertension | 0.1 | 7.97 | 11.02 | 0.04 | 1.38 |
| COPD Smokers No hypertension N = 7 | 0.10 | 6.84 | 19.64 | 0.11 | 2.87 |
| COPD Smokers Hypertension N = 3 | 0.30 | 6.01 | 6.12 | 0.05 | 1.01 |

The Leica equipment (image analyser MR 500) translates the stain intensity into a grey scale (0–250), each unit being one pixel. This allows one to quantitate the data accurately.

These data are based on image analysis of the patient. Data is expressed as pixels per unit area of positively stained tissue and the mean of five fields per slide.

As can be taken from these results, the ratio of $AT_1$ distribution in the sub-epithelial and $AT_2$ in epithelial in normal lung tissue is significantly below 1, whereas this ratio is close to or above 1 in diseased lung tissues. The epithelial forms the inner lining of the trachea and the main bronchii. The increase in the $AT_1/AT_2$ receptor ratio in the bronchial sub-epithelial region of the lung from chronic bronchitic patients compared with control is mainly due to raised levels of the $AT_1$ receptor found on the fibroplasts and macrophages surrounding the airways epithelium and reflects the increased levels of inflammation and fibrosis seen in COPD.

The above results clearly demonstrate that $AT_1$ receptors which modulate angiotensin II are located in sub-epithelial lung tissue and especially the distribution in corresponding lung tissue is increased. Accordingly, the inhibition of angiotensin II by means of AT1 receptor antagonists leads to decrease in airways obstruction.

Furthermore, the experiments show that the distribution of $AT_2$ in epithelial lung tissue, especially in corresponding diseased tissue, e.g. mainly on the bronchial epithelial cells, and also in structural cells of the alveola, e.g. on mucous glands of the alveola, is increased. As $AT_2$ receptors are anti-proliferative, anti-fibrotic and pro-apoptotic, their modulation is useful for the treatment of specific forms of lung conditions and diseases, especially for the treatment of adults respiratory distress syndrome (ARDS) and for reducing the proliferative capacity of the epithelium in lung and breast cancer, furthermore, for the treatment of sepsis syndrome, lung injury forms, such as pneumonia, aspiration of gastric content, chest trauma, shock, burns, fat embolia, cardiopulmonary bypass, $O_2$ toxicity, haemorrhagic pancreatitis, interstitial and bronchoalveolar inflammation, proliferation of epithelial and interstitial cells, collagen accumulation, fibrosis.

Receptor distribution in normal breast tissue and in patients with breast cancer The breast specimens included in this study are randomly recruited from the files of the Pathology Dept, University Hospital, Ghent. All have been fixed in formalin, processed into paraffin wax and a diagnosis of their pathological status made by the departmental pathologists. Sixteen cases have been included: 14 invasive ductal carcinomas, one invasive colloid carcinoma and one invasive lobular carcinoma.

Immunocytochemistry is carried out on paraffin wax embedded tissue sections using the polyclonal antibodies for AT1 and AT2 used in the lung study together with the streptavidinbiotin-peroxidase complex method as before.

In order to provide a possible model for testing receptor antagonists, cell lines originating from human breast tissues are also studied for their receptor content. This can provide a useful in vitro working model for further biochemical and cytological studies.

Resuls

The data obtained clearly demonstrate the presence of angiotensin II type 1 and 2 receptors in normal human breast tissue with AT2 being found on the cuboidal epithelium lining the ducts and AT1 predominantly present on the ductal myoepithelial cells. All staining was abolished by omitting the primary antibody from the incubation.

In all cases the connective tissue was positive for the AT1 receptor along with no ($11/16$) to weak ($5/16$) staining of the cancer cells. For the AT2 receptor, the opposite was observed with all carcinomas being positive and almost no stromal reactivity ($1/16$).

Results from the cell lines tested were very interesting with a different staining pattern being seen in each one. The short term cultures of normal mammary epithelial cells were strongly positive for the AT1 receptor but stained only weakly for the AT2 receptor.

| | | Breast carcinomas | | | |
|---|---|---|---|---|---|
| | | $AT_1$ | | $AT_2$ | |
| Patient | Breast Carcinoma | Carcinoma | Stroma | Carcinoma | Stroma |
| 1 | invasive, interm. differentiated ductal carcinoma - grade 2 Bloom-Richardson classification | − | ++ | ++ | − |
| 2 | invasive, interm. differentiated ductal adenocarcinoma | − | +++ | ++ focal | − |
| 3 | invasive, poorly differentiated ductal carcinoma - ductal carcinoma in situ | − | ++ | + | − |
| 4 | invasive, interm. differentiated ductal carcinoma - extensive ductal carcinoma in situ | − | + | ++ | − |
| 5 | invasive colloid carcinoma | − | ++ | ++ | − |
| 6 | invasive, interm. differentiated ductal carcinoma - ductal carcinoma in situ | + | + | +++ | − |
| 7 | invasive, well differentiated ductal carcinoma - large ductal carcinoma in situ | − | ++ | ++ | − |
| 8 | invasive, poorly differentiated ductal ductal carcinoma - ductal carcinoma in situ | + | ++ | +++ | − |
| 9 | invasive, well differentiated ductal carcinoma | − | + | ++ focal | − |
| 10 | invasive, poorly differentiated ductal carcinoma - ductal carcinoma in situ | − | + | + | − |
| 11 | invasive, poorly differentiated ductal carcinoma - multifocal carcinomas in situ | − | ++ | ++ | − |
| 12 | invasive, poorly differentiated ductal carcinoma | − | +++ | ++ | + |
| 13 | invasive, poorly differentiated invasive carcinoma | + | ++ | ++ | − |
| 14 | invasive, poorly differentiated ductal carcinoma - several ducal carcinomas in situ | − | ++ focal | ++ | − |
| 15 | invasive, poorly differentiated ductal carcinoma - several ductal carcinomas in situ | + | +++ | + | − |
| 16 | invasive, lobular carcinoma - cribriform intraductal carcinoma | + | + | + | − |

As can be seen from these results, the presence of the AT1 receptor on normal epithelial cells appears to be very different to the lung. However, the epithelial cell type is myoepithelial whereas the AT2 receptor in both tissues is found on cuboidal epithelial cells. At the same time, the positive stromal staining for the AT1 receptor is the same for both tissues. The latter is clearly linked to the presence of fibroblasts in the extracellular matrix.

The presence of the AT2 receptor on the carcinoma cells and in such a widespread and reproducible manner is surprising. The cell types described here carrying the specific receptors provide an ideal in vitro model for such studies.

These experiments clearly demonstrate the surprising effect that in the instant model using breast carcinoma cells, the $AT_1$ receptors are mainly distributed in the stroma while the $AT_2$ receptors could mainly be ascertained in the carcinoma cells.

All these surprising results clearly demonstrate that any $AT_1$ receptor antagonist or $AT_2$ receptor modulator may be used for the treatment of conditions or diseases associated with the increase of $AT_1$ receptors in the sub-epithelial area or increase of $AT_2$ receptors in the epithelia, especially for the treatment of obstructive airways diseases. Obstructive airways diseases a classification of respiratory diseases which are characterized by decreased airway size and increased airway secretion, resulting in reduced alveolar ventilation. Obstructive airways diseases comprise reversible and irreversible conditions and are selected, for example, from chronic obstructive pulmonary disease, such as bronchitis, e.g. chronic bronchitis and emphysema, likewise from asthma, cystic fibrosis, interstitial lung disease, invasive lung cancer, pulmonary vascular disease, and increased resistance to airflow during forced expiration. Any such treatment may also, but not necessarily, be associated with the treatment of hypertension as well as both non-smokers and smokers.

These surprising results clearly demonstrate that any $AT_2$ receptor modulator may be used for the treatment of conditions or diseases associated with an increase of $AT_2$ receptors in epithelial lung tissue, especially for the treatment of specific forms of lung conditions and diseases, especially for the treatment of adults respiratory distress syndrome (ARDS) and for reducing the proliferative capacity of the epithelium in invasive lung cancer, furthermore, for the treatment of sepsis syndrome, lung injury forms, such as pneumonia, aspiration of gastric content, chest trauma, shock, burns, fat embolia, cardiopulmonary bypass, $O_2$ toxicity, haemorhagic pancreatitis, interstitial and broncho-alveolar inflammation, proliferation of epithelial and interstitial cells, collagen accumulation, fibrosis.

$AT_1$ receptor antagonists or $AT_2$ receptor modulator are agents that modify the host's biological response to tumor cells with resulting therapeutic benefit. The increased $AT_1$ receptor expression in mammary ductal myoepithelium and of the $AT_2$ receptor in mammary cuboidal epithelium demonstrate that any $AT_1$ receptor antagonist or $AT_2$ receptor modulator may be used for treatment of invasive breast carcinoma. These included scirrhous, infiltrative, papillary, ductal, medullary and lobular breast cancers as well as metastasis in the lungs, pleura, skeleton and liver. Treatment should be considered as adjuvant therapy in combination with surgery, radiotherapy or as palliative therapy with hormonal therapy or other biological response modifiers such as interferons, interleukins, tumor necrosis factors, monoclonal antibodies etc.

While clinical examination and mammography suggest breast cancer, it is only the examination of the tissue biopsy which allow to make the diagnosis. The distribution pattern of $AT_1$ and $AT_2$ receptors can be used as marker for hyperplasia (location of $AT_1$ receptors) and for invasive cancer (location of $AT_2$ receptors) and therefore for the diagnostic of the malignancy of the tumor. $AT_1$ receptor antagonists include compounds having differing structural features. For example, mention may be made of the compounds which are listed in the European Patent Application having the publication No. 443983 (EP 443983), in particular in the compound claims and the final products of the working examples, the subject-matter of which claims is hereby incorporated into the present application by reference to this publication.

Preference is given to (S)-N-(1-carboxy-2-methylprop-1-yl)-N-pentanoyl-N-[2'(1H-tetrazol-5-yl)biphenyl-4-ylmethyl ]amine [Valsartan] of the formula (I)

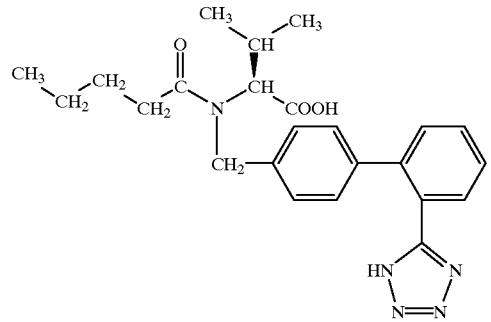

and its pharmaceutically utilizable salts.

Furthermore, the compounds which are listed in European Patent Application having the publication No. 253310 (EP 253310), in particular in the compound claims and the final products of the working examples, are hereby incorporated into the present application by reference to this publication.

Preference is given to the compound [Losartan] of the following formula

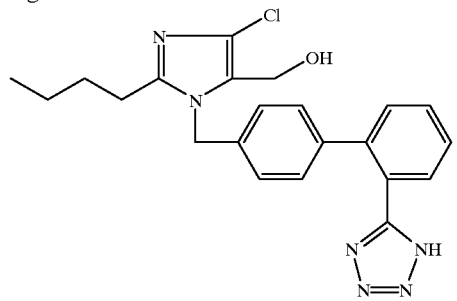

and its pharmaceutically utilizable salts.

Furthermore, the compounds listed in the European Patent Application having the publication No. 403159 (EP 403159), in particular in the compound claims and the final products of the working examples, are hereby incorporated into the present application by reference to this publication.

Preference is given to the compound [Eprosartan] of the following formula

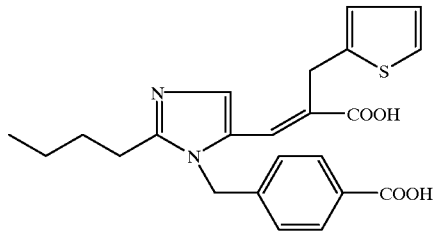

and its pharmaceutically utilizable salts.

Furthermore, the compounds listed in the PCT Patent Application having the publication No. WO 91/14679, in particular in the compound claims and the final products of the working examples, are hereby incorporated into the present application by reference to this publication.

Preference is given to the compound [Irbesartan] of the following formula

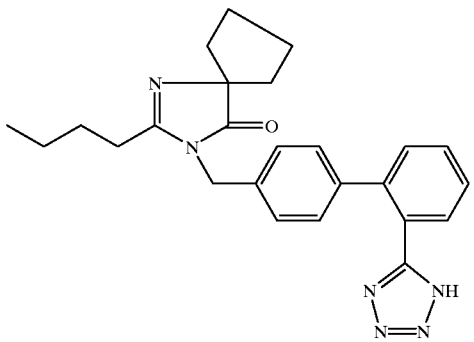

and its pharmaceutically utilizable salts.

Furthermore, the compounds listed in the European Patent Application having the publication No. EP 420237 (EP 420237), in particular in the compound claims and the final products of the working examples, are hereby incorporated into the present application by reference to this publication.

Preference is given to the compound [E-1477] of the following formula

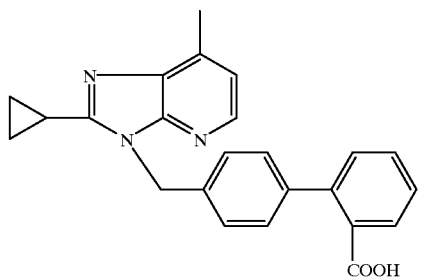

and its pharmaceutically utilizable salts.

Furthermore, the compounds listed in the European Patent Application having the publication No. 502314 (EP 502314), in particular in the compound claims and the final products of the working examples, are hereby incorporated into the present application by reference to this publication.

Preference is given to the compound [Telmisartan] of the following formula

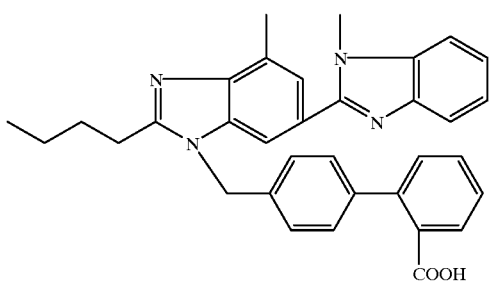

and its pharmaceutically utilizable salts.

Furthermore, the compounds listed in the European Patent Application having the publication No. 459136 (EP 459136), in particular in the compound claims and the final products of the working examples, are hereby incorporated into the present application by reference to this publication.

Preference is given to the compound [Candesartan] of the following formula

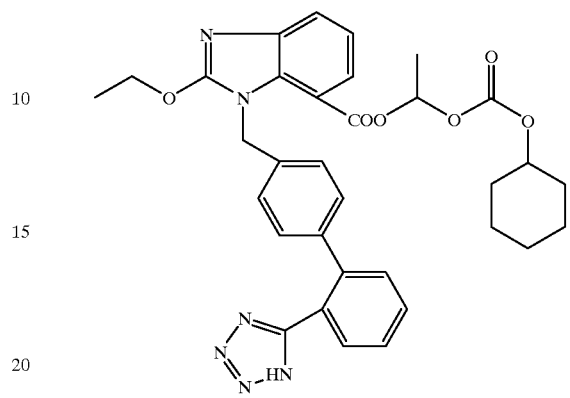

and its pharmaceutically utilizable salts.

Furthermore, the compounds listed in European Patent Application having the publication No. 504888 (EP 504888), in particular in the compound claims and the final products of the working examples, are hereby incorporated into the present application by reference to this publication.

Preference is given to the compound [SC-52458] of the following formula

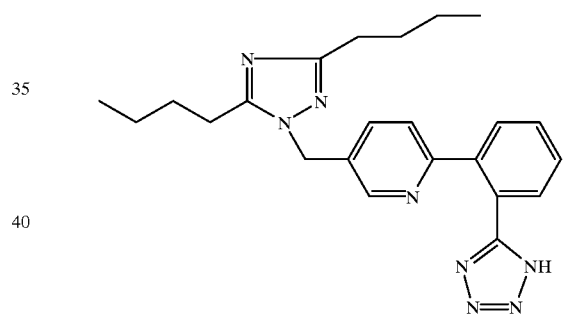

and its pharmaceutically utilizable salts.

Furthermore, the compounds listed in the European Patent Application having the publication No. 514198 (EP 514198), in particular in the compound claims and the final products of the working examples, are hereby incorporated into the present application by reference to this publication.

Preference is given to the compound [Saprisartan] of the following formula

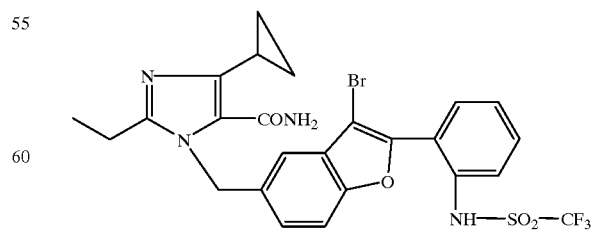

and its pharmaceutically utilizable salts.

Furthermore, the compounds listed in the European Patent Application having the publication No. 475206 (EP 475206), in particular in the compound claims and the final products of the working examples, are hereby incorporated into the present application by reference to this publication.

Preference is given to the compound of the following formula

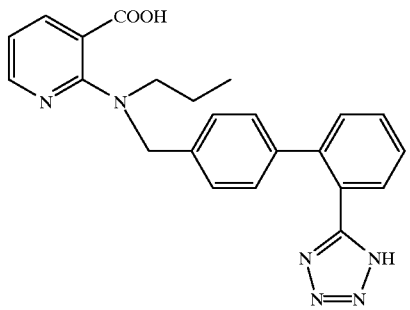

and its pharmaceutically utilizable salts.

Furthermore, the compounds listed in the PCT Patent Application having the publication No. WO 93/20816, in particular in the compound claims and the final products of the working examples, are hereby incorporated into the present application by reference to this publication.

Preference is given to the compound [ZD-8731] of the following formula

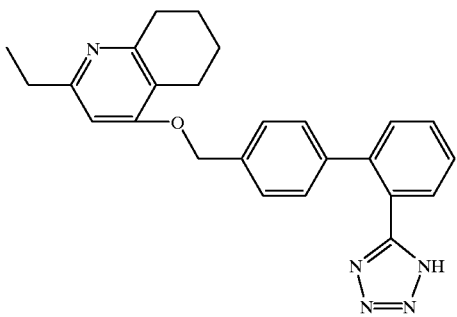

and its pharmaceutically utilizable salts.

$AT_2$ receptor ligands (modulators) include compounds having differing structural features. For example, mention may be made of the compounds which are listed in WO 94/13651, in particular in the compound claims and the final products of the working examples, the subject-matter of which claims is hereby incorporated into the present application by reference to this publication.

Furthermore, the compounds listed in WO 94/13642, in particular in the compound claims and the final products of the working examples, are hereby incorporated into the present application by reference to this publication.

$AT_1$ receptor antagonists or $AT_2$ receptor ligands, respectively, which, for example, possess at least one basic centre can form acid addition salts. These are formed, for example, using strong inorganic acids, such as mineral acids, e.g. sulfuric acid, a phosphoric acid or a hydrohalic acid, using strong organic carboxylic acids, such as $C_1$–$C_4$ alkanecarboxylic acids which are unsubstituted or substituted, for example, by halogen, e.g. acetic acid, such as saturated or unsaturated dicarboxylic acids, e.g. oxalic, malonic, succinic, maleic, fumaric, phthalic or terephthalic acid, such as hydroxycarboxylic acids, e.g. ascorbic, glycolic, lactic, malic, tartaric or citric acid, such as amino acids, e.g. aspartic or glutamic acid, or such as benzoic acid, or using organic sulfonic acids, such as $C_1$–$C_4$ alkanesulfonic acids or arylsulfonic acids which are unsubstituted or substituted, for example, by halogen, e.g. methanesulfonic acid or p-toluenesulfonic acid. Examples of suitable salts with bases are metal salts, such as alkali metal or alkaline earth metal salts, e.g. sodium, potassium or magnesium salts, or salts with ammonia or an organic amine, such as morpholine, thiomorpholine, piperidine, pyrrolidine, a mono-, di- or tri-lower alkyl amine, e.g. ethyl-, tert-butyl-, diethyl-, diisopropyl-, triethyl-, tributyl- or dimethylpropyl-amines, or a mono-, di- or tri-hydroxy lower alkyl amine, e.g. mono-, di- or tri-ethanolamine. Furthermore, corresponding internal salts can be formed.

The invention provides pharmaceutical preparations, which comprise an $AT_1$ receptor antagonist or an $AT_2$ receptor modulator, respectively, or a pharmaceutically acceptable salt thereof, for the treatment of conditions or diseases associated with the increase of AT1 receptors in the sub-epithelial area or increase of $AT_2$ receptors in the epithelia.

The invention also provides the use of an $AT_1$ receptor antagonist or or an $AT_2$ receptor modulator, respectively, or a pharmaceutically acceptable salt thereof, for producing a pharmaceutical preparation for the treatment of conditions or diseases associated with the increase of $AT_1$ receptors in the sub-epithelial area or increase of $AT_2$ receptors in the epithelia.

The invention furthermore provides a method for the treatment of conditions or diseases associated with the increase of $AT_1$ receptors in the sub-epithelial area or increase of $AT_2$ receptors in the epithelia, which comprises administering a therapeutically effective amount of an $AT_1$ receptor antagonist or an $AT_2$ receptor modulator, respectively, or a pharmaceutically acceptable salt thereof.

The invention also provides the use of an $AT_1$ receptor antagonist or an $AT_2$ receptor modulator, respectively, or a pharmaceutically acceptable salt thereof, for the treatment of conditions or diseases associated with the increase of $AT_1$ receptors in the sub-epithelial area or increase of $AT_2$ receptors in the epithelia.

These pharmaceutical preparations are for enteral, such as oral, and also rectal or parenteral, administration to homeotherms, with the preparations comprising the pharmacological active compound either alone or together with customary pharmaceutical auxiliary substances. For example, the pharmaceutical preparations consist of from about 0.1% to 100%, preferably of from about 1% to about 80%, of the active compound. Pharmaceutical preparations for enteral or parenteral, and also for ocular, administration are, for example, in unit dose forms, such as coated tablets, tablets, capsules or suppositories and also ampoules. These are prepared in a manner which is known per se, for example using conventional mixing, granulation, coating, solubulizing or lyophilizing processes. Thus, pharmaceutical preparations for oral use can be obtained by combining the active compound with solid excipients, if desired granulating a mixture which has been obtained, and, if required or necessary, processing the mixture or granulate into tablets or coated tablet cores after having added suitable auxiliary substances.

The dosage of the active compound can depend on a variety of factors, such as mode of administration, homeothermic species, age and/or individual condition. Normally, in the case of oral administration, an approximate daily dose of from about 10 mg to about 360 mg, for example in the case of Valsartan e.g. of about 40 mg, 80 mg, 160 mg or 320 mg, is to be estimated for a patient of approximately 75 kg in weight.

A further aspect of the present invention are solid oral dosage forms of valsartan which may be used for the treatment of diseases and conditions e.g. as disclosed hereinbefore.

WO 97/49394 (the content of which is incorporated herein by reference, especially (but not limited to) the subject mattter as claimed) discloses compressed solid oral dosage forms, e.g., by compaction, of valsartan (optionally in salt form) optionally combined with hydrochlorothiazide (HCTZ). In WO 97/49394 the preferred range of cellulose is given as 10 to 30%, e.g., 21%, for valsartan/HCTZ compositions and 5% Valsartan alone. The preferred range of crosslinked polyvinylpyrolidone (Crospovidone) is given as 10 to 20%, e.g., 13%.

After exhaustive testing it has been found surprisingly that it is possible to improve the bioavailability characteristics of known solid formulations of valsartan by increasing the proportion of microcristalline cellulose. It has also been found surprisingly that it is possible to improve the quality, e.g., better weight uniformity and better compression for the tablets, of said known solid formulations of Valsartan by decreasing the proportion of crosslinked PVP crospovidone.

Thus, in a further aspect, the present invention relates to a solid oral dosage form comprising valsartan as the active agent and more than 30% of microcristalline cellulose by weight based on the total weight of the core components of said solid oral dosage form, e.g., 31 to 65%, e.g., 50%.

In a further aspect, the present invention relates to a solid oral dosage form comprising valsartan as the active agent and microcristalline cellulose wherein the weight ratio of valsartan to microcristalline cellulose is from 2.5: 1 to 0.3: 1, e.g., 2: 1 to 1: 1, e.g., 1.4: 1.

In a further embodiment the solid oral dosage form of the invention comprises less than 13% of crospovidone, e.g., 2 to 10%, by weight based on the total weight of the core components of the solid oral dosage form.

Preferably, the weight ratio of valsartan to Crospovidone is from 7:1 to 3:1, e.g., 6:1 to 4:1, e.g., 5.3:1.

Preferably, the weight ratio of microcristalline cellulose to crospovidone is from 7:1 to 1:1, e.g., 4:1 to 2:1, e.g., 3.6:1.

The solid oral dosage form according to the invention may comprise from 20 to 360 mg of valsartan, e.g., 40, 80, 160, 320mg. With this range of dosages treatment flexibility and efficacy, e.g., in blood pressure reduction, may be increased.

In a further aspect, the invention relates to a solid oral dosage form comprising
- 20 to 65% of valsartan
- 31 to 65% of microcristalline cellulose
- 2 to 13% of crospovidone.

A typical composition may comprise:
- 20 to 65% of valsartan
- 31 to 50% of microcristalline cellulose
- 2 to 10% of crospovidone
- 1 to 10% of magnesium stearate
- 0.5 to 5% of colloidal anhydrous silica.

If desired 1 to 10% by weight of the core composition, e.g., 5 to 10%, of Cutina, or 1 to 10% by weight of the core composition, e.g., 5 to 10% of stearic acid may be added.

Preferably solid oral dosage forms of the invention is in the form of a compressed tablet.

In a further aspect the invention relates to a solid oral dosage form, e.g., a compressed tablet, comprising more than 250 mg and up to 360 mg, e.g., 320 mg, of Valsartan as an active agent.

Other excipients as lubricants and glidants commonly used in solid oral formulations may be used and reference is made to the extensive literature on suitable substances, see in particular Fiedler's "Lexicon der Hilfstoffe", 4th Edition, ECV Aulendorf 1996 and "Handbook of Pharmaceutical Excipients" Wade and Weller Ed.(1 994) the content of which is incorporated herein by reference.

The solid oral dosage forms according to the present invention may be in the form of dragèes in which case the solid oral dosage form is provided with a coating typically a sugar, shellac or other film coating entirely conventional in the art. Attention is drawn to the numerous known methods of coating employed in the art, e.g. spray coating in a fluidized bed, e.g. by the known methods using apparatus available from Aeromatic, Glatt, Wurster or Hüttlin, in a perforated pan by the Accela Cota method, or to the submerged sword coating method. The additives commonly used in confectioning are employed in such methods. For example, coatings which may be used are those disclosed in WO 97/49394, Opadry and the like.

The pharmaceutical compositions of the present invention are useful in the known indications of the particular active agent incorporated therein.

The exact dose of active agent and the particular formulation to be adminstered depend on a number of factors, e.g. the condition to be treated, the desired duration of the treatment and the rate of release of the active agent. For example, the amount of the active agent required and the release rate thereof may be determined on the basis of known in vitro or in vivo techniques, determining how long a particular active agent concentration in the blood plasma remains at an acceptable level for a therapeutic effect.

For example, the composition of the invention in clinical trials has a comparable bioavailability to the commercial form of Diovan®.

Preferably the dissolution rate of solid form according to the present invention is above 90% over 30 minutes.

For example dosages in the range of 10 mg to 360 mg of valsartan per day for a 755 kilogram mammal, e.g., humans, and in standard animal models, may be used. An excellent tolerability of valsartan provided by the compositions may be observed in standard animal tests and in clinical trials.

The invention provides in another of its aspects a process of making a solid oral dosage form as hereinabove described. Such solid oral dosage form may be produced by working up components as in WO 97/49394 (herein incorporated by reference), e.g. as defined hereinabove, in appropriate amounts, to form unit dosage forms.

For example there is provided a process of making the solid oral dosage forms as hereinabove described comprising the steps of
i) grinding the active agent and pharmaceutically acceptable additives,
ii) subjecting a mixture of the ground active agent and additives to compression to form a coprimate (the compacted mass)
iii) converting the coprimate to form a granulate and
iv) compressing the granulate to form the solid oral dosage form.

The process is carried out in the absence of water, i.e. it is a dry compression method. The process may be carried out under ambient conditions of temperature and humidity; it is not necessary to ensure that the process is carried out in a dry atmosphere.

The initial grinding step i) may be carried out according to conventional milling methods or micronisation methods. The active agent and the additives can be milled either individually or together to particle sizes from about 0.1 micrometers ($\mu$g) to about 1500$\mu$, e.g., 1.0$\mu$ to 900$\mu$, e.g., 60μ to 600μ. At least 90% of the crystals of both the active agent and the additives are present in these ranges. Particles of this size are obtained by conventional comminution methods, e.g. grinding in an air jet mill, hammer and screen mill, fine impact mill, ball mill or vibrator mill.

Micronisation is preferably effected by known methods using an ultrasonic disintegrator, e.g. of the BRANSON Sonifier type, or by stirring a suspension with a high speed agitator, for example with a stirrer of the HOMOREX type.

The ground particles may optionally at this stage be sieved and mixed according to known methods.

Compression to form a coprimate requires the compaction of the dry ground components. Compaction may be carried out using a slugging technique or preferably, roller compaction. Roller compaction apparatus is conventional and essentially utilises two rollers which roll towards each other. A hydraulic ram forces one of the rollers against the other to exert a compacting force against the ground particles fed into the roller compactor via a screw conveyor system.

A compaction force of between 25 and 65 kN, e.g., 25 and 45 kN may be used. Within this range of compaction forces it has surprisingly been found that for each particular formulation a minimum compaction force should be used in order to obtain a solid oral dosage form wherein the granulate disintegrates into discrete primary particles at a desirable rate, e.g. disintegration occurs approximately six times faster for a solid oral dosage form compressed above a minimum compaction force. Such a rapid disintegration rate is unusual for tablets and is similar to the disintegration rate of a capsule formulation. The particular minimum compaction force is dependent on the active agent content in any given formulation and therefore also depends on the amount and nature of the additives present.

Given this information, the skilled addressee would clearly be able to determine the minimum compaction force for other formulations using routine experimentation and without undue burden.

The roller speed may be set at between 1 and 20 rpm and preferably 9 to 15 rpm. After passing through the rollers the compacted mass (the coprimate) resembles a thin ribbon in segments.

The coprimate may be screened and or milled to produce the granulate. Screening in its simplest form involves the passing of the coprimate emerging from the rollers through a seive under mechanical pressure. More preferably, the coprimate is screened using an oscillating mill, e.g. a MGI 624 Frewitt (Key International Inc.).

The compression of the granulates to tablet cores can be carried out in a conventional tabletting machine, e.g. in an EK-0 Korsch eccentric tabletting machine or a rotary compression machine, e.g., at a compression greater than 2 kN. The tablet cores may vary in shape and be, for example, round, oval, oblong, cylindrical or any other suitable shape, and may also vary in size depending on the concentration of the therapeutic agents. A characteristic of tablets according to the invention is their small size having regard to the amount of active agent contained therein.

In a preferred embodiment of the invention tablets obtained by the compression method described above are slightly oval. The edges of the tablets may be bevelled or rounded.

In a particularly preferred embodiment of the invention a solid oral dosage form is compressed in the form of a tablet having an oblong shape in which the ratio of dimensions length:width:height is, e.g., 2.5–5.0: 0.9–2.0: 1.0, and preferably in which the base and top face of the tablet independently of one another are planar or convexly curved about the longitudinal axis; the side faces are planar, the end faces can be of any shape and the edges are optionally bevelled or rounded.

In a particularly preferred embodiment of the invention a solid oral dosage form is compressed, from the granulate, in the form of a tablet of oblong shape in which the length is approximately 10.0 to 15.0 mm, the width approximately 5.0 to 6.0 mm and the height approximately 3.0 to 4.0 mm.

In another particularly preferred embodiment of the invention a solid oral dosage form is compressed from granulates in the form of a tablet of oblong shape in which the length is approximately 15.0 to 18.0 mm, the width approximately 6.0 to 9.0 mm and the height approximately 3.5 to 5.0 mm.

In yet another preferred embodiment of the invention there is provided a tablet which is essentially disc-shaped with the upper and lower faces having a slightly convex surface. Preferably the tablet has a diameter of about 8 to 8.5 mm and a depth of about 3 to 3.5 mm, or a diameter of about 16 mm and a depth of about 6 mm. The tablets may occupy a volume from about 0.1 $cm^3$ to about 1 $cm^3$, e.g., 0.1 $cm^3$ to about 0.45 $cm^3$, e.g., 0.2 to 0.3 $cm^3$, e.g about 0.125 $cm^3$ or 0.25 $cm^3$.

They may furthermore be transparent, colourless or coloured and also marked so as to impart to this product an individual appearance and to make them instantly recognizable. The use of dyes can serve to enhance the appearance as well as to identify the compositions. Dyes suitable for use in pharmacy typically include carotinoids, iron oxides or chlorophyll.

The following examples illustrate the above-described invention; however, it is not intended to restrict the scope of this invention in any manner.

FORMULATION EXAMPLE 1

| Film-Coated Tablets | | |
|---|---|---|
| Components | Compostion Per Unit (mg) | Standards |
| Granulation | | |
| Valsartan [= active ingredient] | 80.00 | |
| Microcrystalline cellulose/ Avicel PH 102 | 54.00 | NF, Ph. Eur |
| Crospovidone | 20.00 | NF, Ph. Eur |
| Colloidal anhydrous silica/ colloidal silicon dioxide/Aerosil 200 | 0.75 | Ph. Eur/NF |
| Magnesium stearate | 2.5 | NF, Ph. Eur |
| Blending | | |
| Colloidal anhydrous silica/ colloidal silicon dioxide/Aerosil 200 | 0.75 | Ph. Eur/NF |
| Magnesium stearate | 2.00 | NF, Ph. Eur |
| Coating | | |
| Purified water*⁾ | — | |
| DIOLACK pale red 00F34899 | 7.00 | |
| Total tablet mass | 167.00 | |

*⁾Removed during processing.

The film-coated tablet is manufactured e.g. as follows:

A mixture of valsartan, microcrystalline cellulose, crospovidone, part of the colloidal anhydrous silica/colloidal silicon dioxide/Aerosile 200, silicon dioxide and magnesium stearate is premixed in a diffusion mixer and then sieve through a screnning mill. The resulting mixture is again pre-mixed in a diffusion mixer, compacted in a roller compacter and then sieve through a screening mill. To the resulting mixture, the rest of the colloidal anhydrous silica/colloidal silicon dioxide/Aerosile 200 are added and the final blend is made in a diffusion mixer. The whole mixture is compressed in a rotary tabletting machine and the tabletts are coated with a film by using Diolack pale red in a perforated pan.

FORMULATION EXAMPLE 2

Film-coated tablets

| Components | Compostion Per Unit (mg) | Standards |
|---|---|---|
| Granulation | | |
| Valsartan [= active ingredient] | 160.00 | |
| Microcrystalline cellulose/ Avicel PH 102 | 108.00 | NF, Ph. Eur |
| Crospovidone | 40.00 | NF, Ph. Eur |
| Colloidal anhydrous silica/ colloidal silicon dioxide/Aerosil 200 | 1.50 | Ph. Eur/NF |
| Magnesium stearate | 5.00 | NF, Ph. Eur |
| Blending | | |
| Colloidal anhydrous silica/ colloidal silicon dioxide/Aerosil 200 | 1.50 | Ph. Eur/NF |
| Magnesium stearate | 4.00 | NF, Ph. Eur |
| Coating | | |
| Opadry Light Brown 00F33172 | 10.00 | |
| Total tablet mass | 330.00 | |

The film-coated tablet is manufactured e.g. as described in Formulation Example 1.

FORMULATION EXAMPLE 3

Film-coated tablets

| Components | Compostion Per Unit (mg) | Standards |
|---|---|---|
| Core: Internal phase | | |
| Valsartan [= active ingredient] | 40.00 | |
| Silica, colloidal anhydrous (Colloidal silicon dioxide) [= Glidant] | 1.00 | Ph. Eur, USP/NF |
| Magnesium stearate [= Lubricant] | 2.00 | USP/NF |
| Crospovidone [Disintegrant] | 20.00 | Ph. Eur |
| Microcrystalline cellulose [= Binding agent] | 124.00 | USP/NF |
| External phase | | |
| Silica, colloidal anhydrous, (Colloidal silicon dioxide) [= Glidant] | 1.00 | Ph. Eur, USP/NF |
| Magnesium stearate [Lubricant] | 2.00 | USP/NF |

-continued

Film-coated tablets

| Components | Composition Per Unit (mg) | Standards |
|---|---|---|
| Film coating | | |
| Opadry ® brown OOF 16711*) | 9.40 | |
| Purified Water**) | — | |
| Total tablet mass | 199.44 | |

*)The composition of the Opadry ® brown OOF 16711 coloring agent is tabulated below.
**)Removed during processing Opadry ® Composition

| Ingredient | Approximate % Composition |
|---|---|
| Iron oxide, black (C.I. No. 77499, E 172) | 0.50 |
| Iron oxide, brown (C.I. No. 77499, E 172) | 0.50 |
| Iron oxide, red (C.I. No. 77491, E 172) | 0.50 |
| Iron oxide, yellow (C.I. No. 77492, E 172) | 0.50 |
| Macrogolum (Ph. Eur) | 4.00 |
| Titanium dioxide (C.I. No. 77891, E 171) | 14.00 |
| Hypromellose (Ph. Eur) | 80.00 |

The film-coated tablet is manufactured e.g. as described in Formulation Example 1.

FORMULATION EXAMPLE 4

Capsules

| Components | Compostion Per Unit (mg) |
|---|---|
| Valsartan [= active ingredient] | 80.00 |
| Microcrystalline cellulose | 25.10 |
| Crospovidone | 13.00 |
| Povidone | 12.50 |
| Magnesium stearate | 1.30 |
| Sodium lauryl sulphate | 0.60 |
| Shell | |
| Iron oxide, red (C.I. No. 77491, EC No. E 172) | 0.123 |
| Iron oxide, yellow (C.I. No. 77492, EC No. E 172) | 0.123 |
| Iron oxide, black (C.I. No. 77499, EC No. E 172) | 0.245 |
| Titanium dioxide | 1.540 |
| Gelatin | 74.969 |
| Total tablet mass | 209.50 |

The tablet is manufactured e.g. as follows:

Granulation/Drying

Valsartan and microcrystallin cellulose are spray-granulated in a fluidised bed granulator with a granulating solution consisting of povidone and sodium lauryl sulphate dissolved in purified water. The granulate obtained is dried in a fluidiesd bed dryer.

Milling/Blending

The dried granulate is milled together with crospovidone and magnesium stearate. The mass is then blended in a conical srew type mixer for approximately 10 minutes.

Encapsulation

Teh empty hard gelatin capsules are filled with the blended bulk granules under controlled temperature and humidity conditions. The filed capsules are dedustee, visually inspected, weightchecked and quarantied until by Quality assurance department.

FORMULATION EXAMPLE 5

| Capsules | |
|---|---|
| Components | Compostion Per Unit (mg) |
| Valsartan [= active ingredient] | 160.00 |
| Microcrystalline cellulose | 50.20 |
| Crospovidone | 26.00 |
| Povidone | 25.00 |
| Magnesium stearate | 2.60 |
| Sodium lauryl sulphate | 1.20 |
| Shell | |
| Iron oxide, red (C.I. No. 77491, EC No. E 172) | 0.123 |
| Iron oxide, yellow (C.I. No. 77492, EC No. E 172) | 0.123 |
| Iron oxide, black (C.I. No. 77499, EC No. E 172) | 0.245 |
| Titanium dioxide | 1.540 |
| Gelatin | 74.969 |
| Total tablet mass | 342.00 |

The formulation is manufactured e.g. as described in Formulation Example 4.

FORMULATION EXAMPLE 6

| Hard Gelatine Capsule | |
|---|---|
| Components | Compostion Per Unit (mg) |
| Valsartan [= active ingredient] | 80.00 |
| Sodium laurylsulphate | 0.60 |
| Magnesium stearate | 1.30 |
| Povidone | 12.50 |
| Crospovidone | 13.00 |
| Microcrystalline cellulose | 21.10 |
| Total tablet mass | 130.00 |

EXAMPLES 7 TO 11

| | Example | | | | |
|---|---|---|---|---|---|
| Components | 7 COMPOSITION PER UNIT (mg) | 8 COMPOSITION PER UNIT (mg) | 9 COMPOSITION PER UNIT (mg) | 10 COMPOSITION PER UNIT (mg) | 11 COMPOSITION PER UNIT (mg) |
| Granulation | | | | | |
| Valsartan Drug Substance | 80.000 | 160.000 | 40.000 | 320.000 | 320.000 |
| Microcrystalline Cellulose (NF, Ph. Eur.)/Avicel PH 102 | 54.000 | 108.000 | 27.000 | 216.000 | 216.000 |
| Crospovidone (NF, Ph. Eur.) | 15.000 | 30.000 | 7.500 | 80.000 | 60.000 |
| Colloidal Anhydrous Silica (Ph. Eur.)/Colloidal Silicon Dioxide (NF)/Aerosil 200 | 1.500 | 3.000 | 0.750 | 3.000 | 6.000 |
| Magnesium Stearate (NF, Ph. Eur.) | 3.000 | 6.000 | 1.500 | 10.000 | 12.000 |
| Blending | | | | | |
| Colloidal Anhydrous Silica (Ph. Eur.)/Colloidal Silicon Dioxide (NF)/Aerosil 200 | — | — | — | 3.000 | — |
| Magnesium Stearate, NF, Ph. Eur. | 1.500 | 3.000 | 0.750 | 8.000 | 6.000 |
| Core Weight/mg | 155.000 | 310.000 | 77.500 | 640.000 | 620.000 |
| Coating | — | — | 3.800 | 15.000 | 16.000 |

EXAMPLE 12

Dissolution of film-coated tablets (FCT)

The dissolution acceptance criteria are Q=75% in 30 min (Paddle 50 rpm, phosphate buffer pH 6.8)

|  | Dissolution FCT | | | |
|---|---|---|---|---|
|  | 40 mg<br>− level | Strength<br>+ level | 320 mg<br>− level | Strength<br>+ level |
| Mean [%] | 98 | 97 | 93 | 89 |
| rel. std. [%] | 1.06 | 2.48 | 2.12 | 2.34 |
| min. [%] | 96 | 94 | 90 | 86 |
| Max. [%] | 99 | 99 | 95 | 92 |

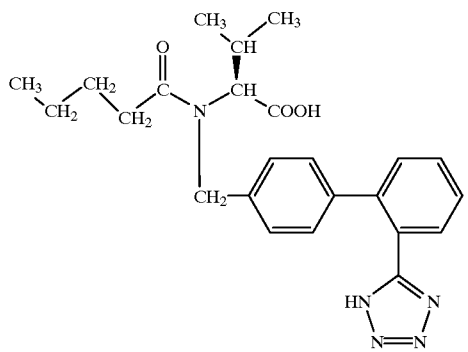

What is claimed is:

1. A method of treating lung cancer comprising administering a therapeutically effective amount of valsartan of formula to a patient in need thereof.

* * * * *